(12) United States Patent
Clay

(10) Patent No.: US 11,730,412 B2
(45) Date of Patent: Aug. 22, 2023

(54) EKG MONITOR AND CABLE MANAGEMENT SYSTEM

(71) Applicant: Heidi D. Clay, Santa Rosa, CA (US)

(72) Inventor: Heidi D. Clay, Santa Rosa, CA (US)

( * ) Notice: Subject to any disclaimer, the term of this patent is extended or adjusted under 35 U.S.C. 154(b) by 688 days.

(21) Appl. No.: 16/946,960

(22) Filed: Jul. 13, 2020

(65) Prior Publication Data

US 2021/0007624 A1    Jan. 14, 2021

Related U.S. Application Data

(60) Provisional application No. 62/873,147, filed on Jul. 11, 2019.

(51) Int. Cl.
*A61B 5/30*   (2021.01)
*G06F 1/16*   (2006.01)
*A61B 5/00*   (2006.01)
*A61B 50/30*  (2016.01)

(52) U.S. Cl.
CPC .............. *A61B 5/303* (2021.01); *A61B 5/002* (2013.01); *A61B 5/6898* (2013.01); *A61B 50/30* (2016.02); *G06F 1/1632* (2013.01); *G06F 1/1656* (2013.01); *A61B 2562/08* (2013.01); *A61B 2562/222* (2013.01)

(58) Field of Classification Search
CPC ....... A61B 5/303; A61B 5/002; A61B 5/6898; A61B 50/30; A61B 2562/08; A61B 2562/222; A61B 2505/01; A61B 5/282; A61B 5/273; A61B 5/30–5/308; A61B 5/318–367; G06F 1/1632; G06F 1/1656
See application file for complete search history.

(56) References Cited

U.S. PATENT DOCUMENTS

| 5,813,979 | A  | * | 9/1998 | Wolfer  | A61B 5/303 |
|           |    |   |        |         | 600/508 |
| 6,205,355 | B1 | * | 3/2001 | Lomanto | A61B 5/303 |
|           |    |   |        |         | 600/509 |

OTHER PUBLICATIONS

Finn, Patrick and Kara, Attila, The Retractable EKG Wiring Unit Major Qualifying Project completed in fulfillment of the Bachelor of Science degree at Worcester Polytechnic Institute Mar. 4, 2016, Worcester, MA Published: Jan. 15, 2020, https://digital.wpi.edu/concern/file_sets/1g05fd215.

* cited by examiner

*Primary Examiner* — Jonathan T Kuo

(57) ABSTRACT

An EKG monitor and cable management system, including a housing, a plurality of retraction reels operably mounted in said housing; and a plurality of EKG leads, each including wires having electrodes disposed at a terminal end, each spooled on one of said reels. The leads deploy and retract in pairs, with the frontal leads retracting as a group of three pairs onto three separate retraction reels.

16 Claims, 5 Drawing Sheets

US 11,730,412 B2

EKG MONITOR AND CABLE MANAGEMENT SYSTEM

CROSS REFERENCES TO RELATED APPLICATIONS

The present application claims the benefit of the filing date of United States Provisional Patent Application Ser. No. 62/873,147, filed Jul. 11, 2019 (Jul. 11, 2019).

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

SEQUENCE LISTING

Not applicable.

BACKGROUND OF THE INVENTION

Field of the Invention

The present invention relates generally to electronic medical devices, and more particularly to cable management systems for electronic medical devices, and still more particularly to a cable management system for a compact portable EKG monitoring system with a cord retraction assembly for retracting wire leads individually or in pairs.

Most medical clinics and hospitals use 12-lead EKG systems for cardiac monitoring. Despite the name, such systems use 10 electrodes applied to the skin of a patient, each electrode connected by a wire to an EKG monitor, comprising a total of 12 measured voltage differences between electrode.

Medical assistants, nurses, technicians, and doctors handling the wires during a procedure often collect and hold the wires in a bunch like a bouquet of wilted flowers, while one at a time each electrode and its connected cable (referred to herein as a "lead") is pulled from the bunch and the electrode attached to the patient's skin, typically using a conducting gel to enhance conduction of the EKG signal. The procedure can be cumbersome and awkward for the nurse or technician and intimidating to the patient: wires dangle and during electrode application can drag around and sometimes across the patient, creating what can be an uncomfortable experience, psychological and physically. For even the most seasoned patient, it can be unpleasant; for an uncomprehending child or a compromised senior, it can dramatically increase stress in an already stressful procedure.

Cable management systems for electronic equipment are known. They include mechanically simple apparatus, such as harnesses and bundling devices (i.e., cable ties, cable wraps, flexible cable conduits) to complex apparatus, such as wire retraction devices. It will be appreciated that wire retraction devices have an advantage over bundling and harness apparatus, in that they can eliminate the problem of having excessive wire in the area in which the device is used. Thus, they provide a viable solution to above-described problem in prior art EKG systems.

For that reason, many power cord retraction devices have been devised, most using a brush contact mechanism to provide a signal path from a power source to an electrical tool or sensor.

Even so, no known cable retraction system exists for an EKG wherein the system includes paired retractable electrode wires coupled to a printed circuit board that sends a Bluetooth signal to an enable tablet or laptop mounted on the system housing.

It would be highly desirable, therefore, to have an EKG wire management system that minimizes the visibility, presence, and handling of the electrode wires during an EKG procedure and that enables a nurse or physician to obtain and record the system on a connected tablet or other portable wireless connected device. Applicant's inventive EKG cable management system provides an elegant and simple solution for health care providers and hospitals.

BRIEF SUMMARY OF THE INVENTION

The present invention addresses the above-described needs by providing an EKG monitor having multiple pairs of retractable wire leads. (As used herein, the term "lead" means a combination of an EKG electrode and a wire or electric cable attached to the electrode.) In embodiments, the leads may be independently deployable and retractable in paired sets, i.e., independently of the other paired sets of leads: arm leads are paired and wound on a first reel; leg leads are paired and spooled on a second reel; and the leads for the intercostal spaces and axillary lines are spooled in pairs on three reels, or six leads forming a cluster.

In the broadest aspect, the monitor includes a base or housing in which are disposed a plurality of retractable reels; viz., five reels for the 12-lead EKG. In further embodiments, the retractable reels are spring-actuated pawl-and-ratchet reels. Each wire of the multi-lead system (typically 10 electrode/wire combinations) is spooled on one of the reels in the system, and in an embodiment, limb leads are paired according to the side of the body to which they will connect (e.g., right arm/left arm=RA/LA and right leg/left leg=RL/LL) and are wound on two separate reels; frontal leads are paired V1 with V2, V3 with V4, and V5 with V6, each pair spooled on a separate reel. The leads pay out from the housing in their respective pairs simply by pulling on the paired leads, and they will retain an extended/locked position as ratchet gears engage pawls. The leads can be extended up to six feet (6 ft.). Retraction of the leads for spooling back on the reels is actuated by release push buttons, which disengage the pawl and thus unlock the reel, and which are color coded and marked according to the placement location. Once retracted, the leads are essentially invisible, secured and concealed within the housing, except for the end portion of the cables and the terminal electrodes, which extend from the housing for easy grasping by a user. The cable management system thereby minimizes the interference of dangling wires during an EKG procedure both on deployment and on retraction for storage after an EKG procedure has been performed.

Each of the paired retractable leads are electrically connected in the EKG housing to a printed circuit board that sends a wireless LAN (e.g., Bluetooth) signal to an enabled tablet or laptop mounted on the system housing. The nurse, physician or technician can obtain and record the system on the connected tablet or other portable wireless connected device, and can thereafter send the data to other health care providers and institutions.

The EKG machine of the present invention is compact, packaged in an attaché-like housing, which allows for quick grab-and-go use, not unlike defibrillation devices. It can be wall mounted for electric charging in office or in an emergency vehicle. It facilitates rapid deployment and rewinding of cables and overall cable management in use. It utilizes Bluetooth or other wireless transmission protocols to send EKG tracings to an installed network connectable device or directly to a designated facility for review via text, email or remotely to a printer. It can be programmed for individualized patient data (i.e., name, date of birth, age, current date, presenting symptom) to be marked on the EKG for tracking (entered by the technician through the user interface.

The inventive EKG machine has several advantages over prior art systems. Most importantly, the EKG machine of the present invention dramatically reduces the time needed for placement of the 10 lead electrodes, and then to acquire and transmit the urgent EKG data to appropriate healthcare providers for review. If and when emergency medical technicians or paramedics are called to a scene to respond to a cardiac emergency, the rapid acquisition and transmission of data can be accomplished from locations far outside the hospital, such as from a patient's home, office, or workplace, doctor's offices, or any public place. The data is streamlined through secure connected networks to enable rapid transmission to an emergency physician for immediate review and appropriate triage, not only to prepare emergency room physicians for treatment as needed, but to direct the patient to a facility most appropriate to the emergency situation.

Such advantages will save lives, as they provide critical improvements in EKG data acquisition and transmission that will yield faster and more well-informed treatment for patients with blocked coronary arteries, thereby improving the chances of survival and reduced comorbidity. Further, because the inventive EKG's can share data expediently with hospital-based healthcare providers from the field, it facilitates critical decision-making with respect to the appropriate facilities most capable of dealing with particular types of cardiac emergencies, i.e., those best suited to the need. This provides a dramatic reduction in the time for the "door to needle" to begin invasive cardiac procedures.

The foregoing summary broadly sets out the more important features of the present invention so that the detailed description that follows may be better understood, and so that the present contributions to the art may be better appreciated. There are additional features of the invention that will be described in the detailed description of the preferred embodiments of the invention which will form the subject matter of the claims appended hereto.

DETAILED DESCRIPTION OF THE INVENTION

Figure 1:
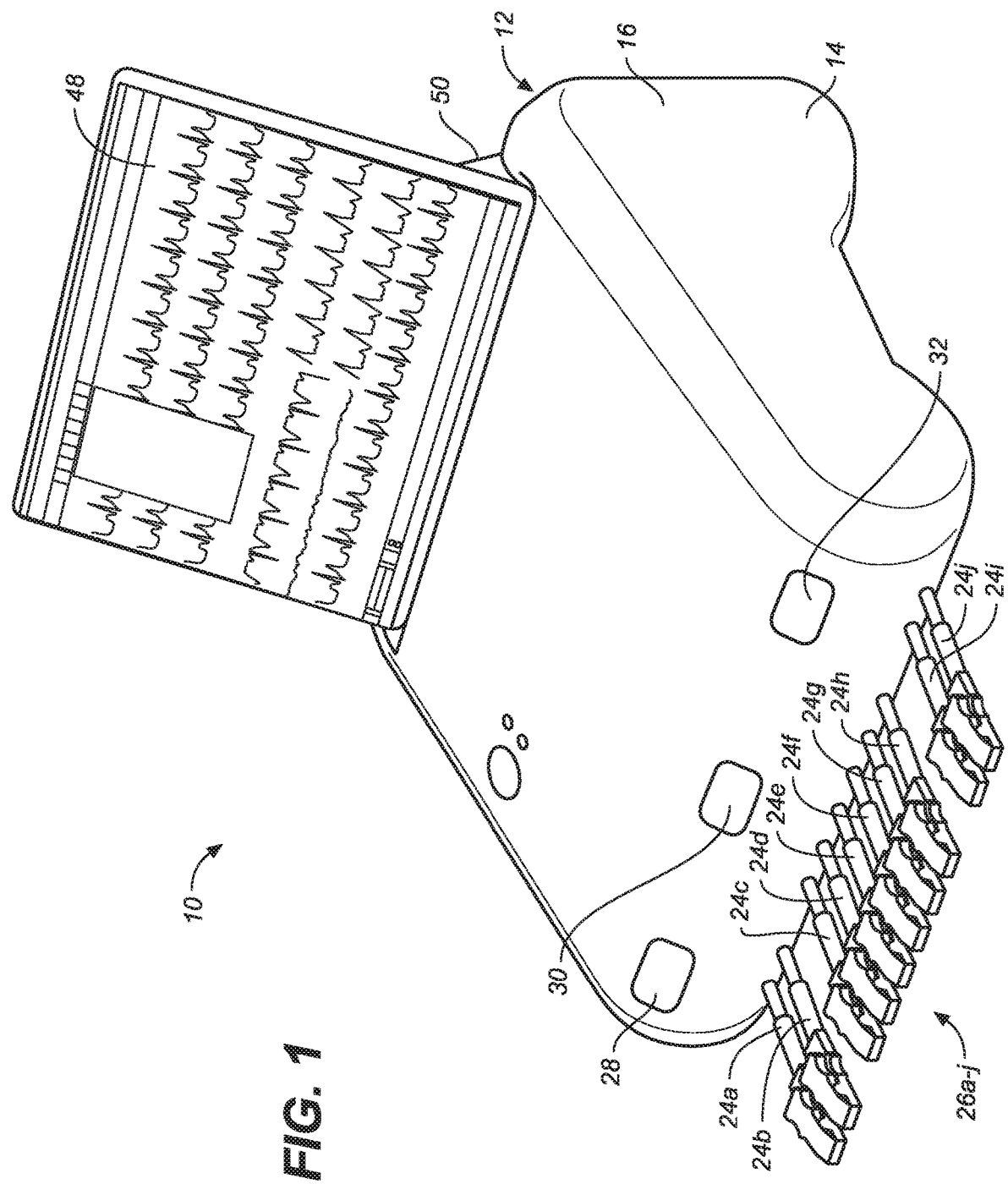
FIG. 1 is an upper front right perspective view of an embodiment of the assembled EKG cable management system of the present invention.
Figure 2:
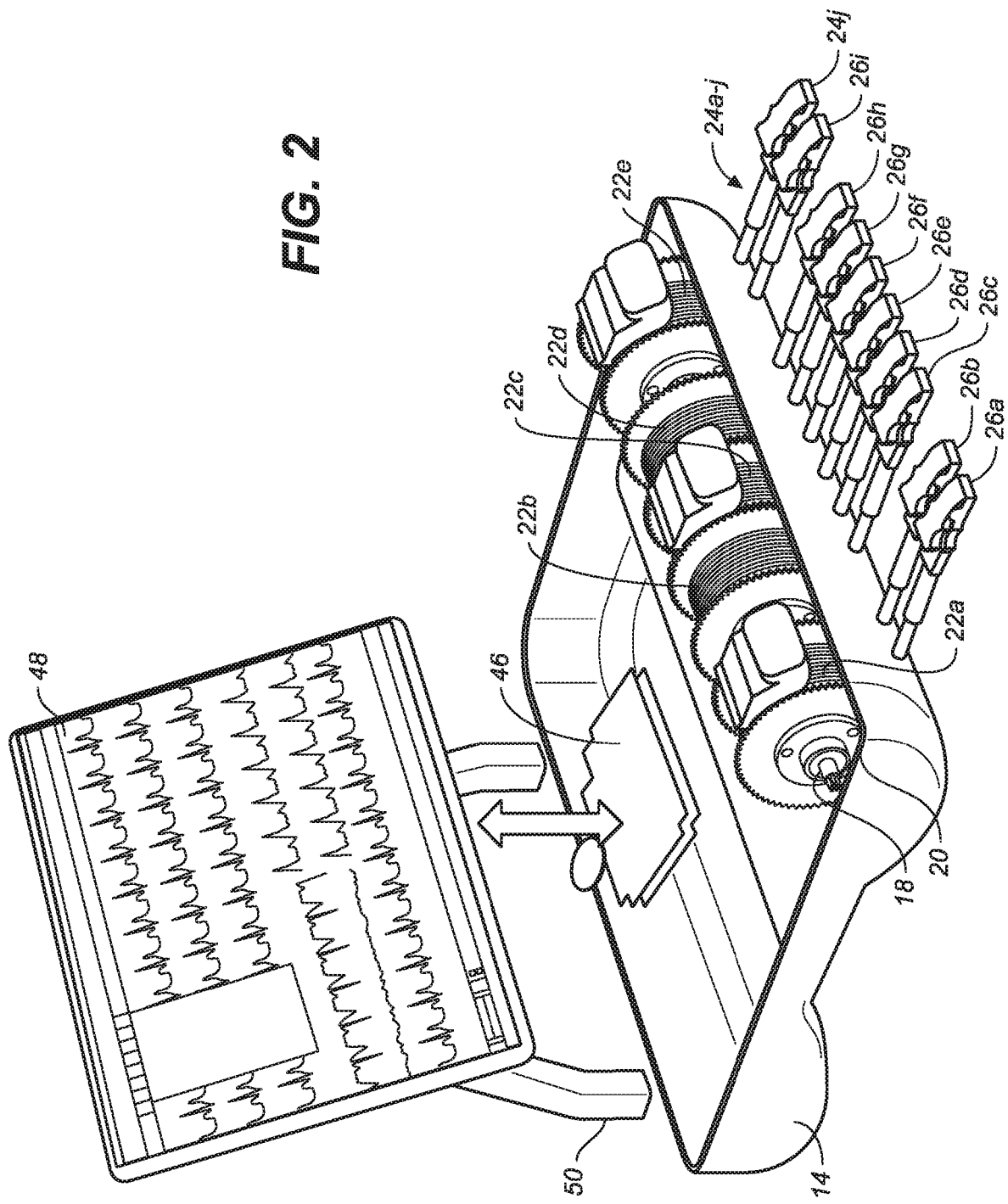
FIG. 2 is an upper front left perspective view showing an alternative embodiment with a upper half of the housing removed to reveal the reeling lead system, PCB, detachable table support, and tablet itself.

The EKG cable management system of the present invention, generally denominated 10 herein, enables medical personnel to monitor the electrical activity of a patient's heart using selectively extended and retracted lead wires. The assembly ensures high quality electrically conductive paths for electrode signals while minimizing device unwieldiness and patient discomfort.

The cable management system in its most essential aspect includes a housing 12, preferably a two-piece snap-together clamshell housing having a base portion 14 and an upper portion 16. Rotatingly mounted on an axle 18, or several coaxially aligned axles journaled in brackets 20 disposed in the base portion, are a plurality of spring-biased spools or reels 22. Rotation of the reels is controlled by a pawl and ratchet assembly, described more fully below, and includes a leftmost (first) reel 22a onto which RA/LA (right and left arm) lead wires 24a, 24b, are wound; a second reel 22b onto which V1 and V2 lead wires 24c, 24d, are wound; a third reel 22c onto which V3 and V4 lead wires 24e, 24f, are wound; a fourth reel 22d on which V5 and V6 lead wires 24g, 24h, are wound; and a fifth, rightmost reel 22e onto which RL/LL (right and left leg) lead wires 24i, 24j, are wound. Each wire includes a terminal electrode 26a-j disposed on the terminal/outer ends of the respective wires. Those with skill will understand that V1 is the lead for the fourth intercostal space on the right sternum; V2 is the lead for placement at the fourth intercostal space at the left sternum; V3 is the lead for placement midway between V2 and V4; V4 is the lead for placement at the fifth intercostal space at the midclavicular line; V5 is the lead for placement at the anterior axillary line at the same level as V4; and V6 is the lead for placement at the mid-axillary line at the same level as V4 and V5.

Figure 3:
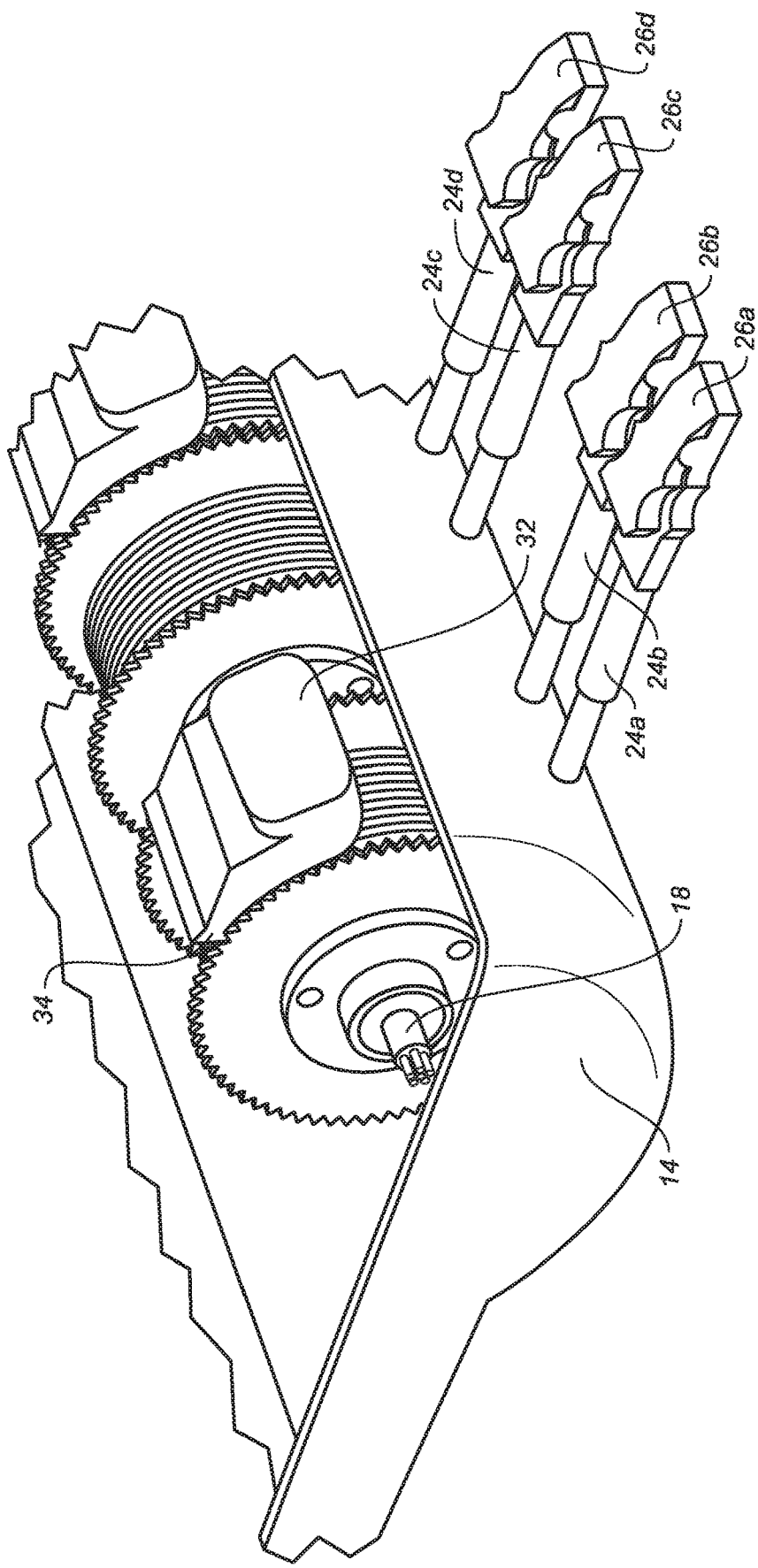
FIG. 3 is an upper left front perspective view showing detail of a portion of the reel system, the particular reels on which are wound wires for the right and left arms and V1-V2.
Figure 4:
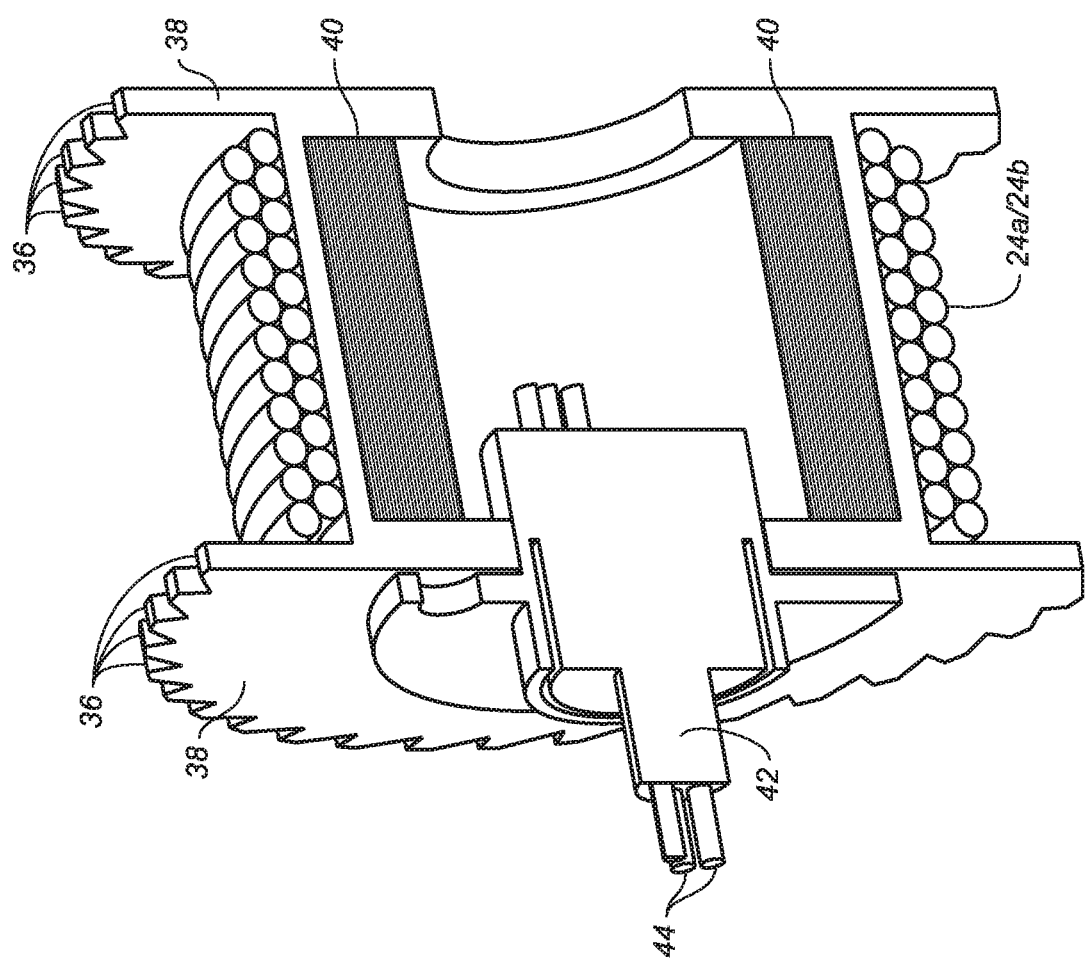
FIG. 4 is a cross-sectional side perspective view of a single reel.
Figure 5:
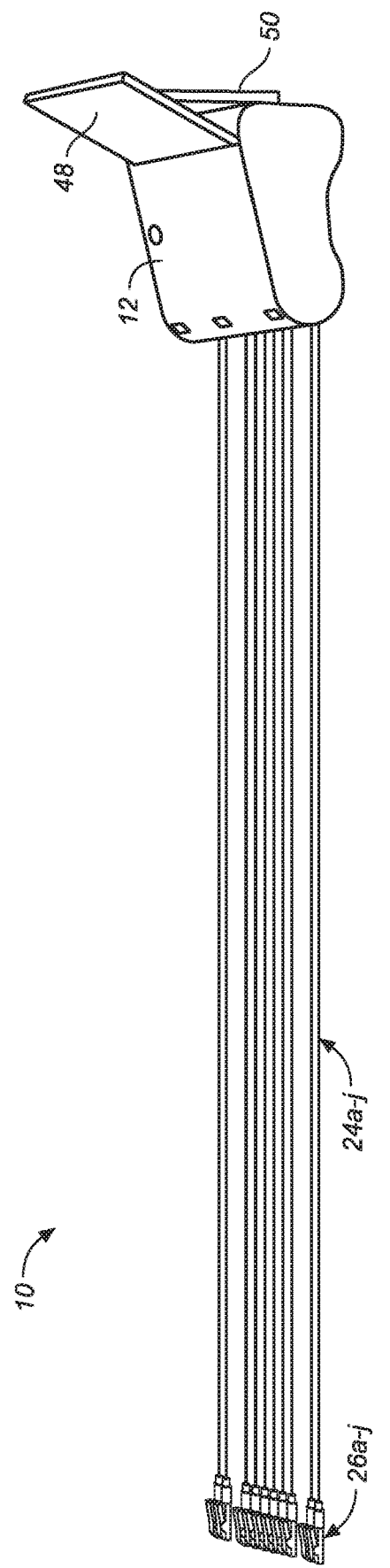
FIG. 5 is an upper right perspective view showing all 10 leads of the 12-lead system fully extended from the housing in a length at which they might be deployed during use.

Each extremity reel 22a, 22e and the frontal lead reels 22b, 22c, 22d, enable selective deployment/extension of the lead wires in pairs when in an unlocked position for deployment, which may be a default setting or accomplished by pushing a push button 28, 30, 32, respectively. The buttons are pivotally mounted above their respective reels and include or otherwise engage a pawl 34 that bears against ratchet gear teeth 36 on a reel gear plate 38 on each reel. [See esp. FIG. 3 for illustration.] The reels pay out individually as the paired sets of the respective lead wires are pulled, and each pair can thus be deployed independently of the others. They are, conversely, urged back (i.e., to retract the lead wires) with a spiral torsion spring 40 brought into increased tension during wire lead pay out, in a manner well-known in the art.

As is thus seen, the reels may be configured with a release button for the paired extremity leads and for the three frontal lead pairs, including paired RA/LA, paired RL/LL, and a cluster of three pairs for the frontal leads, V1/V2, V3/V4, V5/V6. Thus, pushing the RA/LA release button 28 retracts the RA/LA leads, 24a, 24b; pushing the V1-V6 release button 30 retracts frontal V1 through V6 leads, 24c-24h; and pushing the RL/LL release button 32 retracts the RL/LL leads 24i, 24j.

Electrical signal paths are maintained through a conductive slip ring 42 disposed on each reel, which is, in turn, electrically coupled by wires 44 to a printed circuit board 46 having a CPU. The CPU is connected to a wireless transmitter on or proximate the PCB and operating under any of a number of wireless LAN (short range voice and data communications) standards, including, e.g., Wi-Fi (IEEE 802.11b/g/n/ac) or Bluetooth (IEEE 802.15). The CPU is selectively wirelessly connected to a connectable portable electronic device 48, such as a tablet or a smartphone or other mobile device with a mobile operating system, which may be held or mounted and supported on a tablet support 50 attached to the system housing and to which the EKG data may be transmitted.

In embodiments, dimensions of the EKG housing are such as to facilitate portability and transportability. For instance, the housing preferably has a maximum height h at its back side of approximately 6.3 inches, or within a range of approximately 5.5-7.0 inches, and width w of approximately 14.5 inches, or within a useful range of 12.0-16.0 inches, and a depth d of approximately 12.0 inches, or within a useful range of approximately 10.0-14.0 inches. To achieve optimal portability, dimensions at the lower end of the ranges are contemplated.

In this way there is provided a novel and improved EKG monitor and EKG cable management system that achieves all of the objects and advantages set forth above.

The above disclosure is sufficient to enable one of ordinary skill in the art to practice the invention. While this is a full and complete disclosure of the preferred embodiments of this invention, it does not limit the invention to the exact construction, dimensional relationships, and operation shown and described. Various modifications, alternative constructions, changes, and equivalents will readily occur to those skilled in the art and may be employed, as suitable, without departing from the true spirit and scope of the invention. Such changes might involve alternative materials, components, structural arrangements, sizes, shapes, forms, functions, operational features, or the like.

Therefore, the above description and illustrations should not be construed as limiting the scope of the invention, which is defined by the appended claims

What is claimed as invention is:

1. An EKG monitor and cable management system, comprising:
    a housing;
    a plurality of retraction reels operably mounted in said housing; and
    a plurality of EKG leads, each including wires having electrodes disposed at a terminal end, each spooled on one of said reels;
    wherein said leads deploy independently in pairs.

2. The EKG monitor and cable management system of claim 1, wherein each of said leads is independently deployable and retractable in pairs.

3. The EKG monitor and cable management system of claim 2, including upper extremity limb leads paired on a first retraction reel according to the side of the body to which they will connect, three pairs of frontal leads, V1/V2, V3/V4, and V5/V6, spooled in pairs onto second through fourth retraction reels, respectively, and lower extremity limb leads paired on a fifth retraction reel.

4. The EKG monitor and cable management system of claim 3, further including a first release button operatively connected to said first retraction reel, a second release button operatively connected to said second through fourth retraction reels, and a third release button operatively connected to said fifth retraction reel.

5. The EKG monitor and cable management system of claim 4, wherein said reels are spring-actuated pawl-and-ratchet reels.

6. The EKG monitor and cable management system of claim 1, wherein said reels are spring-actuated pawl-and-ratchet reels.

7. The EKG monitor and cable management system of claim 6, wherein each of said reels includes a conductive slip ring electrically connected to a PCB in said housing.

8. The EKG monitor and cable management system of claim 7, wherein said PCB includes a CPU coupled to a wireless transmitter for transmitting EKG data to a mobile device.

9. The EKG monitor and cable management system of claim 8, wherein said housing includes a base and a top which snap together to define a housing interior.

10. The EKG monitor and cable management system of claim 9, wherein said housing includes a tablet mount for supporting a wireless LAN-enabled mobile device.

11. The EKG monitor and cable management system of claim 9, wherein said CPU can be programmed for individualized patient data to be marked on the EKG for tracking.

12. The EKG monitor and cable management system of claim 11, wherein said housing includes a tablet mount for supporting a wireless LAN-enabled mobile device.

13. The EKG monitor and cable management system of claim 12, wherein said CPU can be programmed for individualized patient data to be marked on the EKG for tracking.

14. The EKG monitor and cable management system of claim 8, wherein said CPU can be programmed for individualized patient data to be marked on the EKG for tracking.

15. The EKG monitor and cable management system of claim 1, wherein said plurality of retraction reels includes:
    a first reel onto which right and left arm lead wires are wound;
    a second reel onto which V1 and V2 lead wires are wound;
    a third reel onto which V3 and V4 lead wires are wound;
    a fourth reel on which V5 and V6 lead wires are wound; and
    a fifth, reel onto which right and left leg lead wires are wound.

16. The EKG monitor and cable management system of claim 14, wherein said housing includes a tablet mount for supporting a wireless LAN-enabled mobile device.

\* \* \* \* \*